United States Patent
Liao

(10) Patent No.: US 10,849,565 B2
(45) Date of Patent: Dec. 1, 2020

(54) SCHEMES FOR OBTAINING ESTIMATION OF PHYSIOLOGICAL FEATURE OF SPECIFIC USER, ESTABLISHING PROFILE OF PHYSIOLOGICAL FEATURE OF SPECIFIC USER, AND FOR ESTABLISHING/MANAGING/GRADING PROFILES OF DIFFERENT USERS

(71) Applicant: PixArt Imaging Inc., Hsin-Chu (TW)

(72) Inventor: Yuan-Hsin Liao, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 292 days.

(21) Appl. No.: 15/592,207

(22) Filed: May 11, 2017

(65) Prior Publication Data

US 2018/0325462 A1 Nov. 15, 2018

(51) Int. Cl.
*A61B 5/00* (2006.01)
*A61B 5/021* (2006.01)
*A61B 5/024* (2006.01)

(52) U.S. Cl.
CPC .......... *A61B 5/7271* (2013.01); *A61B 5/0002* (2013.01); *A61B 5/7246* (2013.01); *A61B 5/021* (2013.01); *A61B 5/02416* (2013.01)

(58) Field of Classification Search
CPC ... A61B 5/7271; A61B 5/0002; A61B 5/7246; A61B 5/021; A61B 5/02416; A61B 5/7275
See application file for complete search history.

(56) References Cited

U.S. PATENT DOCUMENTS

| | | | | |
|---|---|---|---|---|
| 2008/0146890 A1* | 6/2008 | LeBoeuf | | A61B 5/0059 600/300 |
| 2008/0146891 A1* | 6/2008 | Wang | | G06F 19/3418 600/300 |
| 2015/0313542 A1* | 11/2015 | Goldberg | | A61B 5/0205 600/384 |
| 2016/0120433 A1* | 5/2016 | Hughes | | A61B 5/6832 600/483 |
| 2016/0242654 A1* | 8/2016 | Quinlan | | A61B 5/1123 |
| 2016/0296160 A1* | 10/2016 | Larson | | A61B 5/1114 |
| 2017/0209055 A1* | 7/2017 | Pantelopoulos | ... | A61B 5/02108 |

* cited by examiner

*Primary Examiner* — Matthew Kremer
*Assistant Examiner* — Avery M Foley
(74) *Attorney, Agent, or Firm* — Winston Hsu

(57) ABSTRACT

A method for obtaining an estimation of a physiological feature of a specific user includes: using a physiological sensor device under a normal sensing mode to sense the physiological feature of the specific user to generate a physiological signal of the normal sensing mode; determining a matched physiological signal from a plurality of test physiological signals by comparing the plurality of test physiological signals with the physiological signal of the normal sensing mode; and calculating a resultant estimation of the physiological feature of the specific user according to the matched physiological signal and the profile of the physiological feature of the specific user.

18 Claims, 6 Drawing Sheets

SCHEMES FOR OBTAINING ESTIMATION OF PHYSIOLOGICAL FEATURE OF SPECIFIC USER, ESTABLISHING PROFILE OF PHYSIOLOGICAL FEATURE OF SPECIFIC USER, AND FOR ESTABLISHING/MANAGING/GRADING PROFILES OF DIFFERENT USERS

BACKGROUND OF THE INVENTION

1. Field of the Invention

The invention relates to a physiological sensing mechanism, and more particularly to method and physiological sensor device for obtaining an estimation of a physiological feature of a specific user, method and physiological sensor device for establishing a profile of a physiological feature of a specific user, and method and system for establishing/managing/grading profiles corresponding to a physiological feature of different users.

2. Description of the Prior Art

Generally speaking, a conventional sensing device may estimate a user's physiological/biological feature such as blood pressure by referring to a physiological signal such as a photoplethysmogram signal. In order to obtain a precise estimation result, it is necessary for the waveform feature of the physiological signal to be clear and stable. However, actually, the waveform of the physiological signal is easily affected by other factors such as an external pressure exerted by a user's finger on a sensing area of conventional sensing device. For example, the conventional sensing device may be configured on a variety of smart phones, and different users can press/touch the sensing area to detect the blood pressure. Since the weights of the variety of smart phones are different and the different users have different operating behaviors or habits, each time the actual pressure exerted on the sensing area of conventional sensor device may be different. Through multiple experiments, the waveform features of physiological signals change and become different in response to externally exerted pressures, even more serious is that the waveform feature of a physiological signal may become unstable and disappear if the externally exerted pressure is too light or too heavy. Further, even the conventional sensor device may be used with a pressure sensor to detect the externally exerted pressure, it is also difficult to obtain a precise estimation result of the physiological feature since different users have different responses and portable device such as smart phones produced by different manufacturers may have different sizes and weights. Also, it is difficult to limit their operating behavior for users. Thus, it is difficult for the conventional sensor device to obtain precise estimation result(s) for a user or for different users.

SUMMARY OF THE INVENTION

Therefore one of the objectives of the invention is to provide method and physiological sensor device for obtaining an estimation of a physiological feature of a specific user, method and physiological sensor device for establishing a profile of a physiological feature of a specific user, and method and system for establishing profiles corresponding to a physiological feature of different users, to solve the above-mentioned problems.

According to embodiments of the invention, a method for obtaining an estimation of a physiological feature of a specific user is disclosed. The method comprises: using a physiological sensor device under a normal sensing mode to sense the physiological feature of the specific user to generate a physiological signal of the normal sensing mode; determining a matched physiological signal from a plurality of test physiological signals by comparing the plurality of test physiological signals with the physiological signal of the normal sensing mode; and, calculating a resultant estimation of the physiological feature of the specific user according to the matched physiological signal and the profile of the physiological feature of the specific user.

According to the embodiments, a method for establishing a profile of a physiological feature of a specific user is further disclosed. The method comprises: using a physiological sensor device under a test sensing mode to sense the physiological feature of the specific user to obtain a plurality of observations for the physiological feature to generate a plurality of test physiological signals respectively; selecting an optimal test physiological signal among the plurality of test physiological signals; calculating a plurality of test estimations of the physiological feature of the specific user according to the plurality of test physiological signals; calculating a plurality of compensation parameters corresponding to the plurality of test physiological signals excluding the optimal test physiological signal by comparing a test estimation of the optimal test physiological signal with a test estimation of each different test physiological signal; and, establishing and storing the profile of the physiological feature of the specific user in the memory circuit according to the plurality of test physiological signals and the plurality of compensation parameters corresponding to the plurality of test physiological signals excluding the optimal test physiological signal.

According to the embodiments, a method for establishing profiles corresponding to a physiological feature of different users is disclosed. The method comprises: using a first physiological sensor device under a test sensing mode to sense the physiological feature of a first user to obtain a plurality of observations for the physiological feature of the first user to generate a plurality of first test physiological signals respectively; establishing a first profile corresponding to the physiological feature of the first user according to the plurality of first test physiological signals; using a second physiological sensor device under the test sensing mode to sense the physiological feature of a second user to obtain a plurality of observations for the physiological feature of the second user to generate a plurality of second test physiological signals respectively; establishing a second profile corresponding to the physiological feature of the second user according to the plurality of second test physiological signals; transmitting the first profile and the second profile to a remote system; and, assigning different grades to the physiological feature of the first user and the physiological feature of the second user according to the first profile and the second profile respectively.

According to the embodiments, a physiological sensor device for obtaining an estimation of a physiological feature of a specific user is disclosed. The physiological sensor device comprises a physiological sensor and a processing circuit. The physiological sensor is configured for operating under a normal sensing mode to sense the physiological feature of the specific user to generate a physiological signal of the normal sensing mode. The processing circuit is coupled to the physiological sensor and is configured for: determining a matched physiological signal from a plurality of test physiological signals by comparing the plurality of test physiological signals with the physiological signal of the normal sensing mode; and, calculating a resultant estimation of the physiological feature of the specific user according to the matched physiological signal and the profile of the physiological feature of the specific user.

According to the embodiments, a physiological sensor device for establishing a profile of a physiological feature of a specific user is disclosed. The physiological sensor device comprises a physiological sensor and a processing circuit. The physiological sensor is configured to operate under a test sensing mode to sense the physiological feature of the specific user to obtain a plurality of observations for the physiological feature to generate a plurality of test physiological signals respectively. The processing circuit is coupled to the physiological sensor and configured for: selecting an optimal test physiological signal among the plurality of test physiological signals; calculating a plurality of test estimations of the physiological feature of the specific user according to the plurality of test physiological signals; calculating a plurality of compensation parameters corresponding to the plurality of test physiological signals excluding the optimal test physiological signal by comparing a test estimation of the optimal test physiological signal with a test estimation of each different test physiological signal; and, establishing and storing the profile of the physiological feature of the specific user in the memory circuit according to the plurality of test physiological signals and the plurality of compensation parameters corresponding to the plurality of test physiological signals excluding the optimal test physiological signal.

According to the embodiments, a system for establishing profiles corresponding to a physiological feature of different users is disclosed. The system comprises a first physiological sensor device, a second physiological sensor device, and a processor. The first physiological sensor device is used for operating under a test sensing mode to sense the physiological feature of a first user to obtain a plurality of observations for the physiological feature of the first user to generate a plurality of first test physiological signals respectively. The second physiological sensor device is used for operating under the test sensing mode to sense the physiological feature of a second user to obtain a plurality of observations for the physiological feature of the second user to generate a plurality of second test physiological signals respectively. The processor is used for establishing a first profile corresponding to the physiological feature of the first user according to the plurality of first test physiological signals, establishing a second profile corresponding to the physiological feature of the second user according to the plurality of second test physiological signals, and assigning different grades to the physiological feature of the first user and the physiological feature of the second user according to the first profile and the second profile respectively.

These and other objectives of the present invention will no doubt become obvious to those of ordinary skill in the art after reading the following detailed description of the preferred embodiment that is illustrated in the various figures and drawings.

DETAILED DESCRIPTION

The mechanism provided by embodiments of the invention is arranged to more accurately obtain an estimation of physiological feature of a specific user by performing only one observation (i.e. one-time observation) for the physiological feature of the specific user wherein the physiological feature for example comprises the user's blood pressure, heart rate, and/or other physiological/biological characteristics. This mechanism is especially useful for obtaining an accurate estimation of the physiological feature under a condition that the physiological feature is not easily detected or estimated due to different user's behaviors. For instance, a conventional physiological sensor device may be used for detecting a user's blood pressure, and the user can touch or press a touch sensing area of the conventional physiological sensor device to sense the user's blood pressure. However, actually, the conventional physiological sensor device needs to perform many observations for the user's blood pressure since the detection result is easily affected by different behaviors of the user (i.e. the user may press or touch the sensing area with different pressures each time). In addition, different users also include different pressing behaviors with different pressures, and the same conventional physiological sensor device may not be suitable for different users. It is difficult to accurately estimate a user's blood pressure by only one observation of the conventional physiological sensor device. The methods and physiological sensor devices provided by the embodiments are to solve the above-mentioned problems. Description is detailed in the following.

Figure 1:
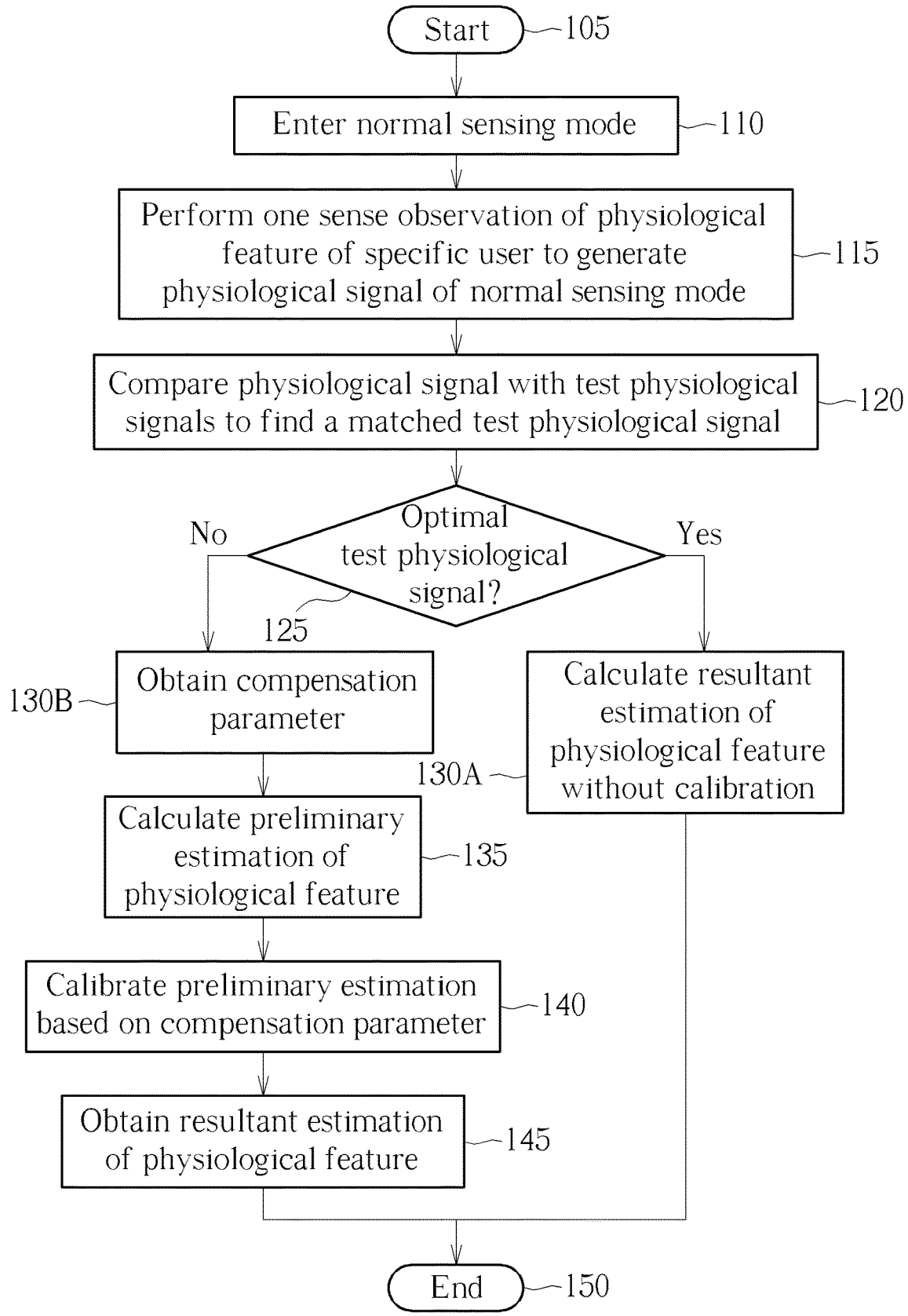
FIG. 1 is a diagram illustrating a flowchart for obtaining an estimation of a physiological feature of a specific user under a normal sensing mode according to a first embodiment of the invention.
Figure 2:
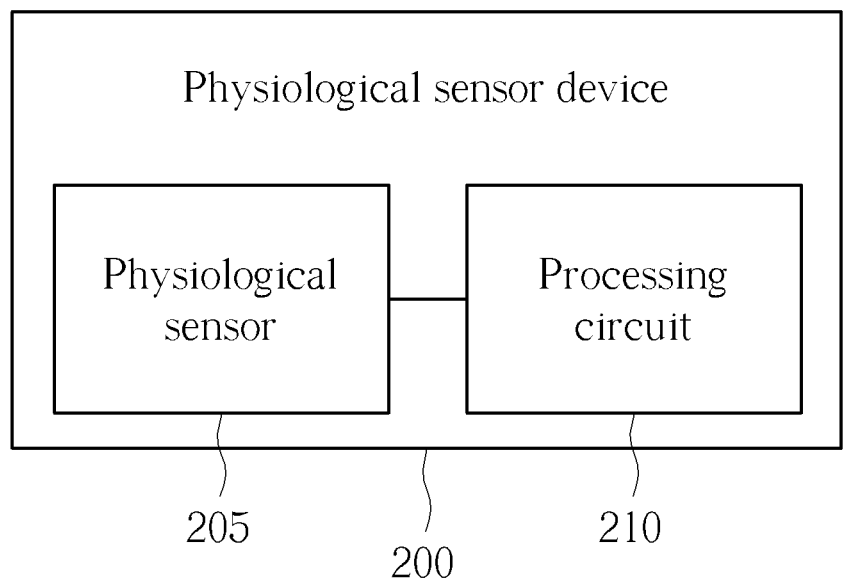
FIG. 2 is a diagram of a physiological sensor device for obtaining an estimation of a physiological feature of a specific user according to the embodiment as shown in FIG. 1.

Refer to FIG. 1 in conjunction with FIG. 2. FIG. 1 is a diagram illustrating a flowchart for obtaining an estimation of a physiological feature of a specific user under a normal sensing mode according to a first embodiment of the invention. FIG. 2 is a diagram of a physiological sensor device 200 for obtaining an estimation of a physiological feature of a specific user according to the embodiment as shown in FIG. 1. The physiological sensor device 200 comprises a physiological sensor 205 and a processing circuit 210 such as a microprocessor, microcontroller, or a processor. The physiological feature of the specific user, for example, indicates a blood pressure of the specific user (but not limited); in other examples, the physiological feature may indicate the heart rate of the user. Provided that substantially the same result is achieved, the steps of the flowchart shown in FIG. 1 need not be in the exact order shown and need not be contiguous, that is, other steps can be intermediate. Steps are detailed in the following:

Step 105: Start;

Step 110: The physiological sensor device 200 enter and operate under the normal sensing mode;

Step 115: Use the physiological sensor device 200 operating under the normal sensing mode to perform one sense observation of the physiological feature of the specific user to generate/obtain a physiological signal of the specific user under the normal sensing mode;

Step 120: Compare the physiological signal of the specific user with a plurality of test physiological signals of the specific user by using the processing circuit 210 to find a matched test physiological signal from the plurality of test physiological signals;

Step 125: Determine whether the matched test physiological signal is an optimal test physiological signal among the test physiological signals. If the matched test physiological signal is an optimal test physiological signal, the flow proceeds to Step 130A, otherwise the flow proceeds to Step 130B;

Step 130A: Calculate a resultant estimation of the physiological feature of the specific user by using the processing circuit 210 according to the matched physiological signal without calibration;

Step 130B: obtain or retrieve a compensation parameter associated with the matched test physiological signal which is not an optimal test physiological signal;

Step 135: Calculate a preliminary estimation of the physiological feature of the specific user by using the processing circuit 210 according to the matched physiological signal;

Step 140: Calibrate or compensate the preliminary estimation of the physiological feature of the specific user by using the processing circuit 210 based on the obtained/retrieved compensation parameter;

Step 145: Obtain or generate a resultant estimation of the physiological feature of the specific user;

Step 150: End.

As mentioned in Step 115, the physiological sensor 205 is configured for operating under the normal sensing mode to sense the physiological feature of the specific user to generate the physiological signal of the normal sensing mode. The processing circuit 210 is coupled to the physiological sensor 205, and is configured for determining the matched physiological signal from the test physiological signals by comparing the test physiological signals with the physiological signal of the normal sensing mode (Step 120), and for calculating a resultant estimation of the physiological feature of the specific user according to the matched physiological signal and a profile of the physiological feature of the specific user (Step 125-Step 145) wherein the profile of the specific user means test physiological signals, compensation parameter(s), and optimal test physiological signal which are associated with such user. Information of different users' profiles is different. Further, a physiological signal for example is a photoplethysmogram signal (but not limited).

The physiological sensor device 200 comprises the normal sensing mode and a test sensing mode. Under the normal sensing mode, the physiological sensor device 200 is used to generate the resultant estimation of the physiological feature for the specific user. Under the test sensing mode, the physiological sensor device 200 is arranged to generate/establish the above-mentioned profile for the specific user.

Figure 3:
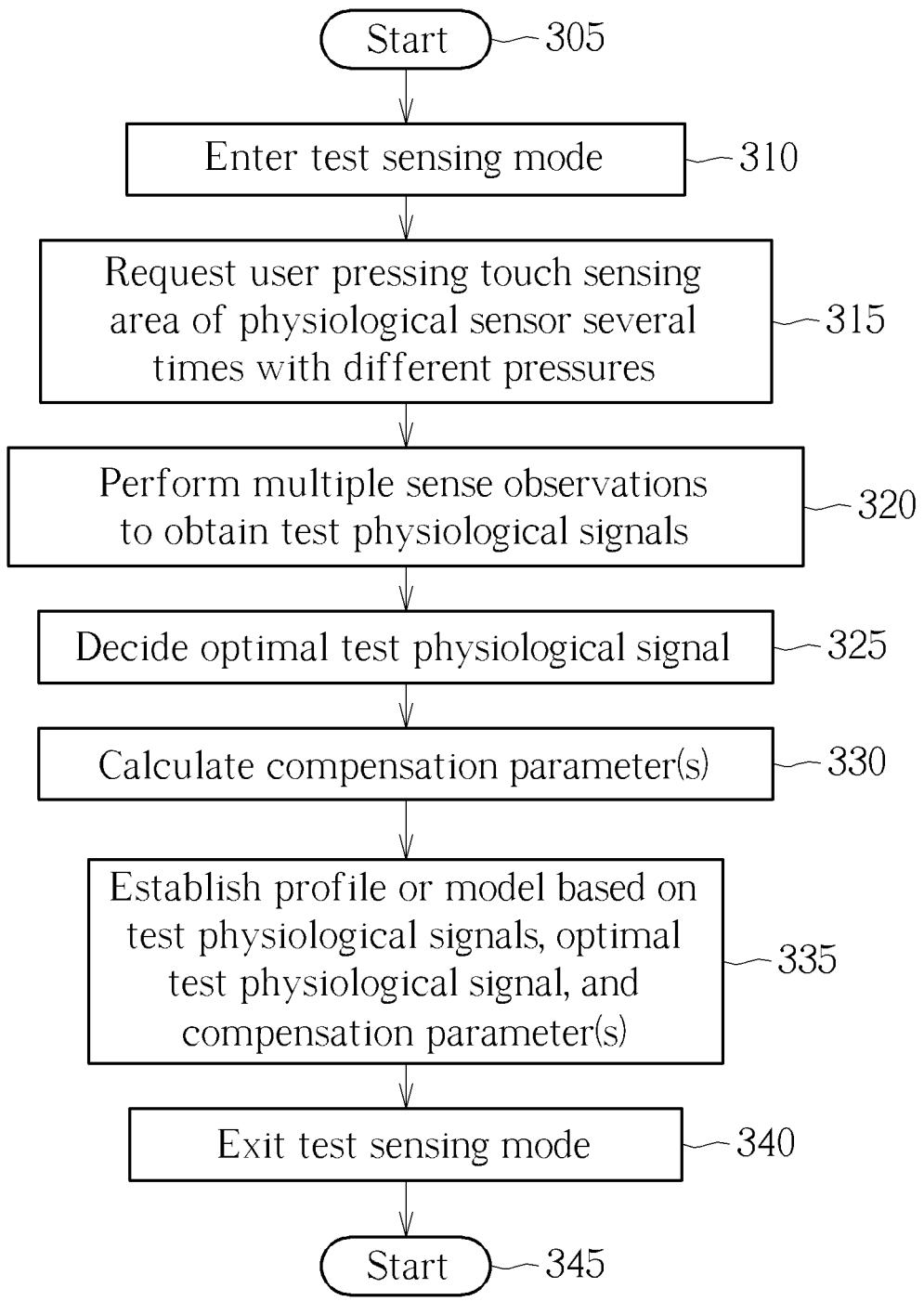
FIG. 3 is a diagram illustrating a flowchart for generating or establishing information of a profile of a specific user under the test sensing mode according to a second embodiment of the invention.
Figure 4:
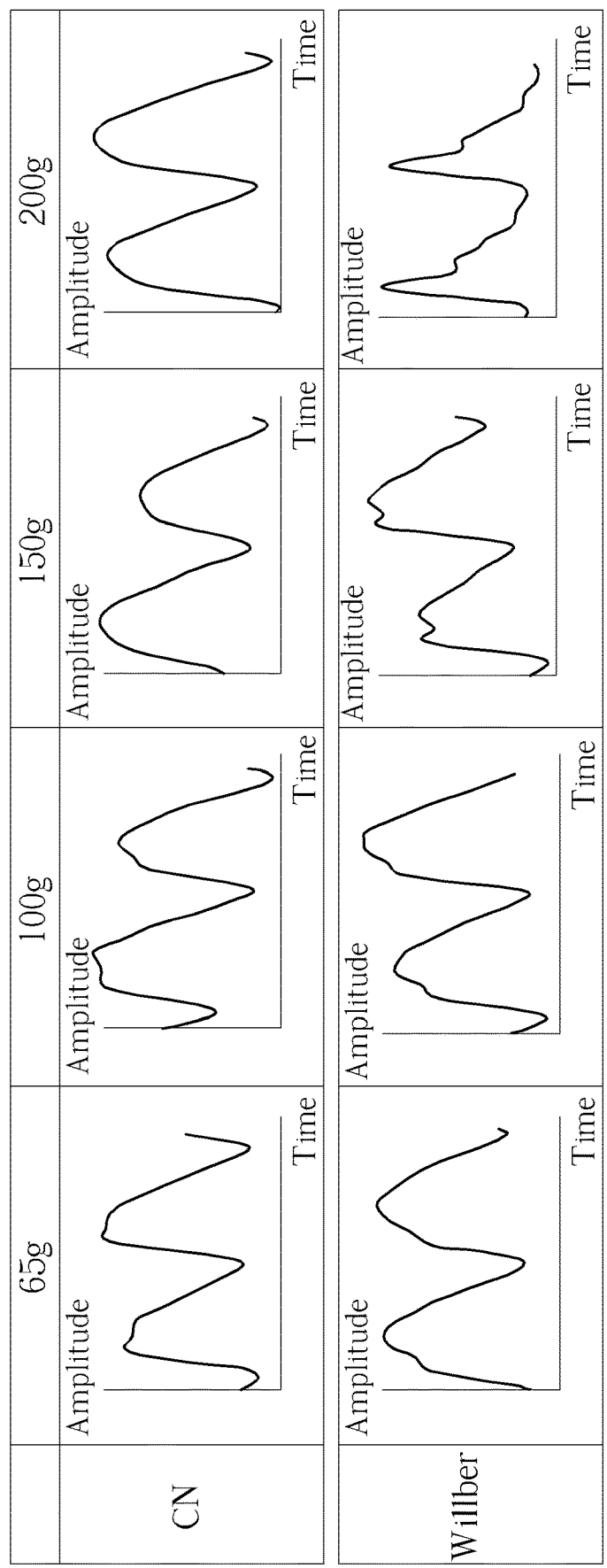
FIG. 4 is a diagram illustrating examples of two different users pressing a touch sensing area of physiological sensor several times by putting different pressures on the touch sensing area.

Refer to FIG. 3 in conjunction with FIG. 4. FIG. 3 is a diagram illustrating a flowchart for generating or establishing information of a profile of a specific user under the test sensing mode according to a second embodiment of the invention. FIG. 4 is a diagram illustrating examples of two different users pressing a touch sensing area of physiological sensor 205 several times by putting different pressures on the touch sensing area. Provided that substantially the same result is achieved, the steps of the flowchart shown in FIG. 3 need not be in the exact order shown and need not be contiguous, that is, other steps can be intermediate. Steps are detailed in the following:

Step 305: Start;

Step 310: The physiological sensor device 200 enter and operate under the test sensing mode;

Step 315: The physiological sensor device 200 via a human-machine interface asks or requests a specific user pressing the touch sensing area of physiological sensor 205 several times with different pressures on the touch sensing area;

Step 320: The physiological sensor 205 performs multiple sense observations to obtain and generate the test physiological signals;

Step 325: The processing circuit 210 decides an optimal test physiological signal from the test physiological signals;

Step 330: The processing circuit 210 calculates/derives compensation parameter(s) corresponding to the other test physiological signals, i.e. the test physiological signals excluding the optimal test physiological signal;

Step 335: The processing circuit 210 establishes and completes the profile or model based on the test physiological signals, optimal test physiological signal, and the compensation parameter(s);

Step 340: Exit the test sensing mode; and

Step 345: End.

Specifically, in Step 315 and Step 320, for example, the physiological sensor device 200 can be further designed with the human-machine interface which is capable of asking a user to touch/press the touch sensing area with different pressures, and the physiological sensor 205 senses the physiological feature of the user several times to obtain a plurality of observations for the physiological feature to generate the test physiological signals respectively. FIG. 4 shows examples of two different users CN and Willber respectively pressing the touch sensing area of physiological sensor 205 by putting different pressures on the touch sensing area. In FIG. 4, the vertical axis means the amplitude of waveform of each physiological signal, and the horizontal axis means the time index.

For instance, in Step 315, the human-machine interface can request a user (CN or Willber) to press the touch sensing area with different pressures four times. As shown by FIG. 4, if the specific user (a current user) is user CN, different patterns of four test physiological signals corresponding to four different pressures such as 65 grams, 100 grams, 150 grams, and 200 grams, respectively asserted/pressed by the users CN, are generated by the physiological sensor 205. Alternatively, if the current user is user Willber, different patterns of another four test physiological signals corresponding to four different pressures such as 65 grams, 100 grams, 150 grams, and 200 grams, respectively asserted/pressed by the users Willber, are generated by the physiological sensor 205. It should be noted that the above-mentioned pressures are not meant to be limitations. Further, it can be seen from different patterns of FIG. 4 that the physiological sensor device 200 can establish different profiles for different users such as users CN and Willber.

In Step 325, the processing circuit 210 selects an optimal test physiological signal among the plurality of test physiological signals. In practice, the processing circuit 210 can determine the optimal test physiological signal based on the waveforms or patterns of test physiological signals. A test physiological signal can be selected as the optimal signal if it is easier or more suitable to use such physiological signal compared to using the other signals to precisely estimate the physiological feature of a user. If more than two test physiological signals are suitable, then either of the test physiological signals can be selected as the optimal test signal. In practice, for example, the processing circuit 210 may select the optimal test physiological signal according to a slope change/reverse of values neighboring to a peak value of each test physiological signal. For instance, as shown in FIG. 4, for the case of the current user being user Willber, four test physiological signals including different patterns are generated wherein the slope of values neighboring to a peak value of a physiological signal corresponding to the pressure of 150 grams clearly changes or reverses from a negative value to a positive value and this may indicate a reflection wave for the blood pressure. Thus, in this example for estimating the physiological feature of blood pressure, the processing circuit 210 is arranged for selecting a physiological signal including a clear/severe slope change/reverse neighboring to or at its peak value as the optimal test physiological signal. However, this is not meant to be a limitation. In another example for estimating other physiological features, the processing circuit 210 can be arranged for selecting a physiological signal having a waveform cycle with more than a particular time period as the optimal test physiological signal.

After determining the optimal test physiological signal, in Step 330, the processing circuit 210 is arranged to calculate compensation parameters corresponding to the other test physiological signals, i.e. all test physiological signals excluding the optimal test physiological signal. For example, the processing circuit 210 generates and calculates three compensation parameters for the test physiological signals associated with the pressures of 65 grams, 100 grams, and 200 grams corresponding to the user Willber. The three compensation parameters are respectively used for calibration or compensation. In practice, the processing circuit 210 may be arranged to calculate a plurality of test estimations (i.e. test estimation results) of test physiological signals, and then generates compensation parameters based on the optimal test physiological signal and a simple linear statistics model/equation. Taking the example of the current user being user Willber, the processing circuit 210 selects the test physiological signal corresponding to the pressure of 150 grams as the optimal test signal, and then based on the selected optimal test signal and the simple linear statistics model/equation the processing circuit 210 for example generates a linear parameter as the compensation parameter of the pressure 200 grams by using the simple linear statistics model/equation to perform calculations upon the test estimations of test physiological signals of pressures 150 grams and 200 grams. Similarly, the processing circuit 210 can generate linear compensation parameters for the pressures 65 grams and 100 grams. It should be noted that the simple linear statistics model/equation may be represented by $A \times \Delta t + B = C$ wherein parameters A and B means fixed or predefined parameters while $\Delta t$ means a time width of pulse wave of a test physiological signal and parameter C means a test estimation result of such test physiological signal. Parameters $\Delta t$ and C are varied with different patterns of different test physiological signals. Based on this simple linear statistics model/equation, the processing circuit 210 can rapidly calculate the corresponding compensation parameters. However, the example of simple linear statistics model/equation is not meant to be a limitation; in other examples, the processing circuit 210 can adopt different algorithms/models/equations to derive the corresponding compensation parameters.

Further, the above-described profile can be established when a portable device carrying the physiological sensor device 200 is enabled/activated and/or after such portable device has been enabled.

Thus, after the profile of a specific user such as user Willber has been established or completed, the physiological sensor device 200 operating under the normal sensing mode can accurately estimate the physiological feature of the user Willber by performing only one sense observation for the user's physiological feature. For example, under the normal sensing mode, if the physiological sensor device 200 generates and obtains a physiological signal which is like to or matched to the optimal test physiological signal such as the test physiological signal corresponding to 150 grams pressed by the user Willber, the processing circuit 210 generate a resultant estimation based on such physiological signal without calibrating or compensating the resultant estimation. If the physiological signal which is like to or matched to the test physiological signal such as the signal corresponding to 200 grams, the processing circuit 210 generates a preliminary estimation based on the physiological signal and then uses the compensation parameter associated with the test physiological signal of the pressure 200 grams to compensate/calibrate the preliminary estimation to generate a resultant estimation. By doing so, when the physiological sensor device 200 operates under the normal sensing mode to detect the blood pressure of a user, no matter how the user presses/touches a touch sensing area of the sensor device 200, the sensor device 200 is capable of generating a precise estimation for the user's blood pressure. That is, under the normal sensing mode, the sensor device 200 can generate the precise/accuracy estimation result for the user's blood pressure by performing only one observation for the physiological feature. This obtains a great performance improvement since a conventional sensor device requires performing multiple observations for the physiological feature to obtain a precise/accuracy estimation result.

Further, the processing circuit 210 may store the profile of the physiological feature of the specific user in the memory circuit, which can be configured within the physiological sensor device 200 or configured outside the physiological sensor device 200. For example, the profile of the physiological feature of the specific user may be stored in a flash memory circuit or a remote system. Additionally, a profile of the physiological feature of the specific user can be stored in an external memory circuit or a remote system and can be downloaded into the physiological sensor device 200, so that the physiological sensor device 200 can obtain the profile information without entering the test sensing mode to generate such information.

Figure 5:
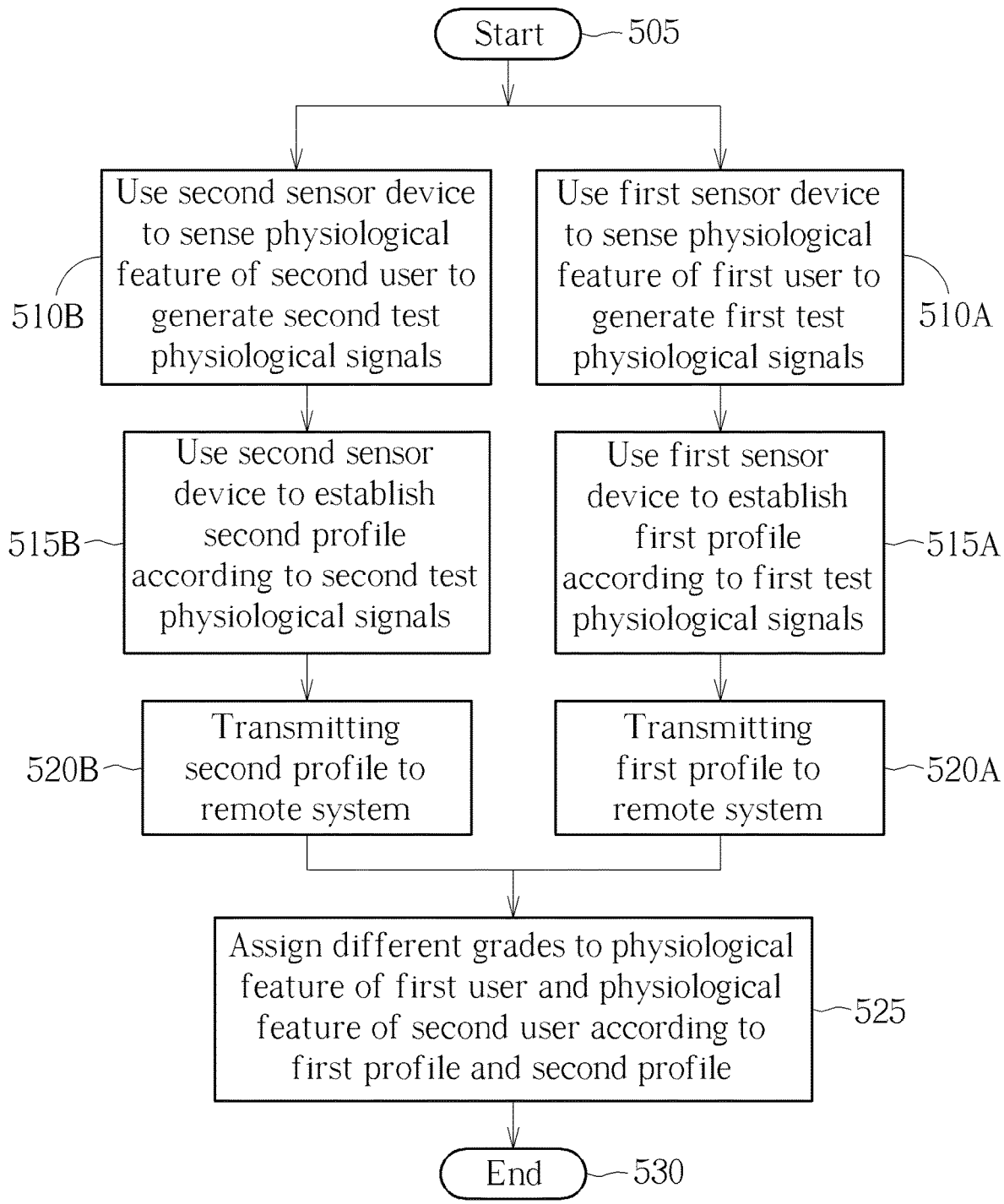
FIG. 5 is a diagram illustrating a flowchart of an example procedure for establishing/managing profiles corresponding to physiological feature(s) of different users according to a third embodiment of the invention.
Figure 6:
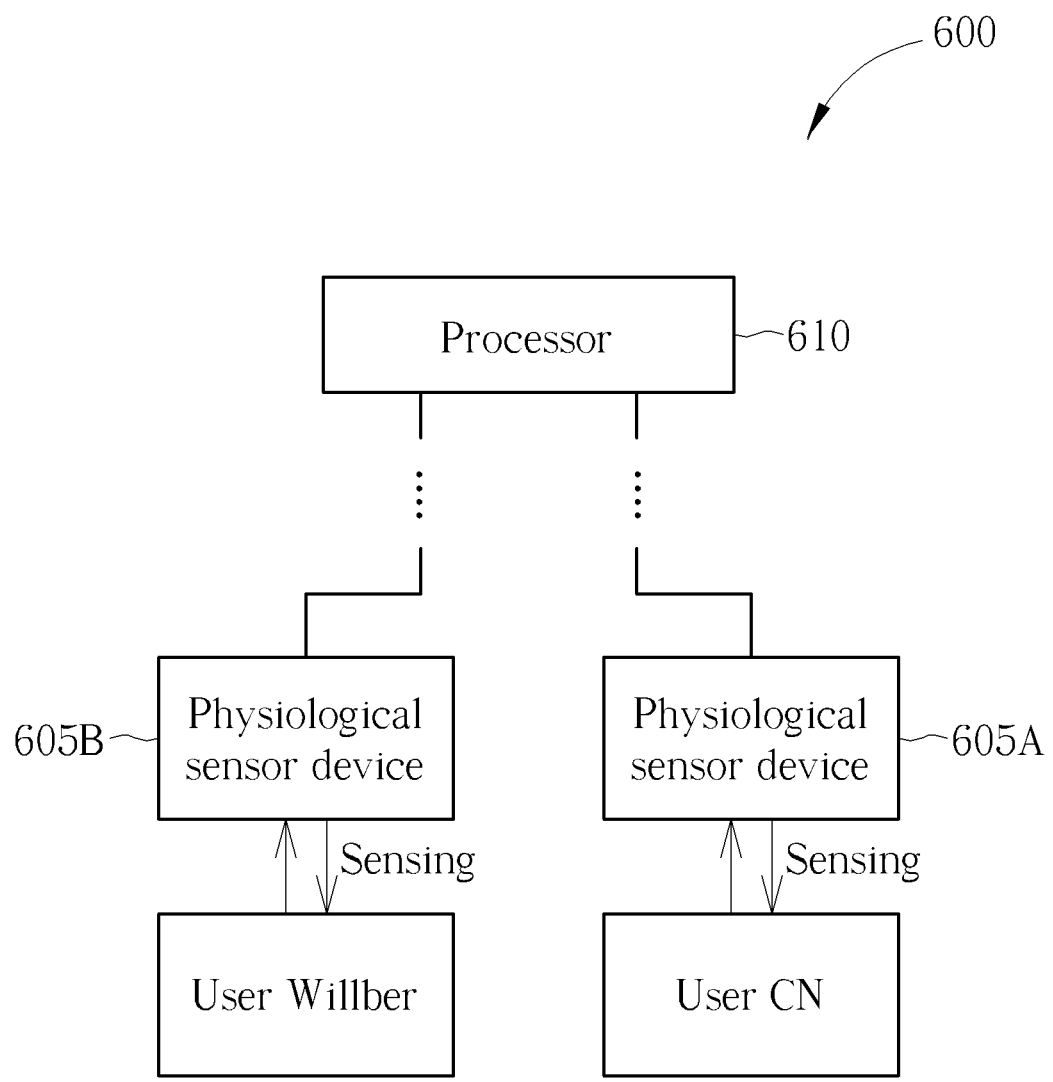
FIG. 6 is a diagram of a system for establishing/managing profiles corresponding to physiological feature(s) of different users according to the embodiment of FIG. 5.

Additionally, in other embodiments, profiles of different users can be transmitted to and managed by a remote system which can assign different grades for different patterns and/or different profiles of the different users for big data analysis. Refer to FIG. 5 in conjunction with FIG. 6. FIG. 5 is a diagram illustrating a flowchart of an example procedure for establishing/managing profiles corresponding to physiological feature(s) of different users according to a third embodiment of the invention. FIG. 6 is a diagram of a system 600 for establishing/managing profiles corresponding to physiological feature(s) of different users according to the embodiment of FIG. 5. The system 600 comprises a processor 610 and at least two physiological sensor devices such as first physiological sensor device 605A and second physiological sensor device 605B which are externally wireless/wire connected to the processor 610. Provided that substantially the same result is achieved, the steps of the flowchart shown in FIG. 5 need not be in the exact order shown and need not be contiguous, that is, other steps can be intermediate. Steps are detailed in the following:

Step 505: Start;

Step 510A: Use the first physiological sensor device 605A under the test sensing mode to sense the physiological feature of a first user such as user CN to obtain a plurality of observations for the physiological feature of the user CN to generate a plurality of first test physiological signals respectively;

Step 510B: Use the second physiological sensor device 605B under the test sensing mode to sense the physiological feature of a second user such as user Willber to obtain a plurality of observations for the physiological feature of user Willber to generate a plurality of second test physiological signals respectively;

Step 515A: Use the first physiological sensor device 605A to establish a first profile corresponding to the physiological feature of the user CN according to the plurality of first test physiological signals;

Step 515B: Use the second physiological sensor device 605B to establish a second profile corresponding to the physiological feature of the user Willber according to the plurality of second test physiological signals;

Step 520A: transmitting the first profile to the processor 610 of remote system 600;

Step 520B: transmitting the second profile to the processor 610 of remote system 600;

Step 525: Use the processor 610 to assigning different grades to the physiological feature of the first user CN and the physiological feature of the second user Willber according to the first profile and the second profile respectively; and Step 530: End.

The operations and functions of physiological sensor devices 605A and 605B are identical to that of physiological sensor device 200 and it not detailed for brevity. In addition, in another embodiment, the operations of Step 515A and Step 515B can be performed by the processor 610 of remote system 600. That is, the physiological sensor devices can directly transmit the information of test physiological signals to the remote processor 610 without generating the profiles, and calculations of the profiles are performed by the processor 610.

To summarize, the invention aims at providing a solution of accurately obtaining an estimation result of the physiological feature of a particular user based on only one observation and his/her unique profile information associated with the physiological feature. In addition, the invention also aims at providing a solution of establishing different unique profiles for the physiological feature of different users and a solution of managing and evaluating different profiles of the physiological feature of different users for big data analysis.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for obtaining an estimation of a physiological feature of a specific user, comprising:

using a physiological sensor device under a normal sensing mode to sense the physiological feature of the specific user to generate a physiological signal of the normal sensing mode;

determining a matched physiological signal from a plurality of test physiological signals by comparing the plurality of test physiological signals with the physiological signal of the normal sensing mode; and calculating a resultant estimation of the physiological feature of the specific user according to the matched physiological signal and a profile of the physiological feature of the specific user;

wherein the profile of the physiological feature of the specific user comprises a plurality of non-optimal test physiological signals in the plurality of test physiological signals, a plurality of compensation parameters of the plurality of non-optimal test physiological signals, and an optimal test physiological signal in the plurality of test physiological signals; the plurality of non-optimal test physiological signals are respectively generated in response to different pressures asserted by the specific user on the physiological sensor device, and the plurality of compensation parameters are associated with the different pressures asserted by the specific user; and, the calculating step comprises:

calculating the resultant estimation of the physiological feature of the specific user according to the matched physiological signal when the matched physiological signal is the optimal test physiological signal; and when the matched physiological signal is a non-optimal test physiological signal in the plurality of test physiological signals and different from the optimal test physiological signal, calculating a preliminary estimation of the physiological feature of the specific user according to the non-optimal test physiological signal and then compensating the preliminary estimation by referring to a compensation parameter corresponding to the non-optimal test physiological signal without using the optimal test physiological signal so as to generate the resultant estimation of the physiological feature of the specific user.

2. The method of claim 1, further comprising:

using the physiological sensor device under a test sensing mode to sense the physiological feature of the specific user to obtain a plurality of observations for the physiological feature to generate the plurality of test physiological signals respectively;

selecting the optimal test physiological signal among the plurality of test physiological signals;

calculating a plurality of test estimations of the physiological feature of the specific user according to the plurality of test physiological signals;

calculating the plurality of compensation parameters corresponding to the plurality of test physiological signals excluding the optimal test physiological signal by comparing a test estimation of the optimal test physiological signal with a test estimation of each different test physiological signal; and establishing and storing the profile of the physiological feature of the specific user in a memory circuit according to the plurality of test physiological signals and the plurality of compensation parameters corresponding to the plurality of test physiological signals excluding the optimal test physiological signal.

3. The method of claim 2, wherein the step of selecting the optimal test physiological signal among the plurality of test physiological signals is to select the optimal test physiological signal according to a slope change of values neighboring to a peak value of each test physiological signal.

4. The method of claim 2, wherein the plurality of observations for the physiological feature of the user corresponds to a plurality of different pressures touched by the specific user for the physiological sensor device.

5. The method of claim 1, wherein the physiological feature of the specific user indicates a blood pressure of the specific user.

6. A method for establishing a profile of a physiological feature of a specific user, comprising:
 using a physiological sensor device under a test sensing mode to sense the physiological feature of the specific user to obtain a plurality of observations for the physiological feature to generate a plurality of test physiological signals respectively;
 selecting an optimal test physiological signal among the plurality of test physiological signals;
 calculating a plurality of test estimations of the physiological feature of the specific user according to the plurality of test physiological signals;
 calculating a plurality of compensation parameters corresponding to a plurality of non-optimal test physiological signals in the plurality of test physiological signals by comparing a test estimation of the optimal test physiological signal with a test estimation of each different non-optimal test physiological signal; and
 establishing and storing the profile of the physiological feature of the specific user in a memory circuit according to the plurality of test physiological signals and the plurality of compensation parameters corresponding to the plurality of non-optimal test physiological signals;
 wherein the profile of the physiological feature of the specific user comprises the plurality of test physiological signals, the plurality of compensation parameters, and the optimal test physiological signal; the plurality of non-optimal test physiological signals in the plurality of test physiological signals are respectively generated in response to different pressures asserted by the specific user on the physiological sensor device, and the plurality of compensation parameters are associated with the different pressures asserted by the specific user; and, a compensation parameter corresponding to a non-optimal test physiological signal is used to compensate a preliminary estimation of the physiological feature of the specific user under a normal sensing mode, and the preliminary estimation is calculated according to the non-optimal test physiological signal.

7. The method of claim 6, wherein the step of selecting the optimal test physiological signal among the plurality of test physiological signals is to select the optimal test physiological signal according to a slope change of values neighboring to a peak value of each test physiological signal.

8. The method of claim 6, further comprising:
 transmitting the profile of the physiological feature of the specific user to a remote system; and
 grading the physiological feature of the specific user at the remote system by comparing the profile of the physiological feature of the specific user with profile(s) of the physiological feature of other different user(s).

9. A method for establishing profiles corresponding to a physiological feature of different users, comprising:
 using a first physiological sensor device under a test sensing mode to sense the physiological feature of a first user to obtain a plurality of observations for the physiological feature of the first user to generate a plurality of first test physiological signals respectively;
 establishing a first profile corresponding to the physiological feature of the first user according to the plurality of first test physiological signals;
 using a second physiological sensor device under the test sensing mode to sense the physiological feature of a second user to obtain a plurality of observations for the physiological feature of the second user to generate a plurality of second test physiological signals respectively;
 establishing a second profile corresponding to the physiological feature of the second user according to the plurality of second test physiological signals; and
 transmitting the first profile and the second profile to a remote system; and
 assigning different grades to the physiological feature of the first user and the physiological feature of the second user according to the first profile and the second profile respectively;
 wherein the first profile comprises the plurality of first test physiological signals, first compensation parameters of a plurality of non-optimal first test physiological signals in the plurality of first test physiological signals, and an optimal first test physiological signal in the plurality of first test physiological signals; the plurality of non-optimal first test physiological signals in the plurality of first test physiological signals are respectively generated in response to different pressures asserted by the first user on the first physiological sensor device, and the first compensation parameters are associated with the different pressures asserted by the first user; the second profile comprises the plurality of second test physiological signals, second compensation parameters of a plurality of non-optimal second test physiological signals in the plurality of second test physiological signals, and an optimal second test physiological signal in the plurality of second test physiological signals; the plurality of non-optimal second test physiological signals in the plurality of second test physiological signals are respectively generated in response to different pressures asserted by the second user on the second physiological sensor device, and the second compensation parameters are associated with the different pressures asserted by the second user; when a matched physiological signal, which is determined from the plurality of first test physiological signals, is the optimal test physiological signal, a resultant estimation of the physiological feature of the first user is calculated according to the matched physiological signal; and, when the matched physiological signal is a non-optimal test physiological signal in the plurality of test physiological signals and different from the optimal test physiological signal, a preliminary estimation of the physiological feature of the first user is calculated according to the non-optimal test physiological signal, and then the preliminary estimation is compensated by referring to a compensation parameter corresponding to the non-optimal test physiological signal without using the optimal test physiological signal so as to generate the resultant estimation of the physiological feature of the first user.

10. A physiological sensor device for obtaining an estimation of a physiological feature of a specific user, comprising:
 a physiological sensor, configured for operating under a normal sensing mode to sense the physiological feature of the specific user to generate a physiological signal of the normal sensing mode; and a processing circuit, coupled to the physiological sensor, configured for:
  determining a matched physiological signal from a plurality of test physiological signals by comparing the plurality of test physiological signals with the physiological signal of the normal sensing mode; and
  calculating a resultant estimation of the physiological feature of the specific user according to the matched physiological signal and the profile of the physiological feature of the specific user;
wherein the profile of the physiological feature of the specific user comprises the plurality of test physiological signals, a plurality of compensation parameters of a plurality of non-optimal test physiological signals in the plurality of test physiological signals, and an optimal test physiological signal in the plurality of test physiological signals; the plurality of non-optimal test physiological signals are respectively generated in response to different pressures asserted by the specific user on the physiological sensor device, and the plurality of compensation parameters are associated with the different pressures asserted by the specific user; when the matched physiological signal is the optimal test physiological signal, the processing circuit is arranged for calculating the resultant estimation of the physiological feature of the specific user according to the matched physiological signal; and, when the matched physiological signal is a non-optimal test physiological signal in the plurality of test physiological signals and different from the optimal test physiological signal, the processing circuit is arranged for calculating a preliminary estimation of the physiological feature of the specific user according to the non-optimal test physiological signal and then for compensating the preliminary estimation by referring to a compensation parameter corresponding to the non-optimal test physiological signal without using the optimal test physiological signal so as to generate the resultant estimation of the physiological feature of the specific user.

11. The physiological sensor device of claim 10, wherein the physiological sensor further operates under a test sensing mode to sense the physiological feature of the specific user to obtain a plurality of observations for the physiological feature to generate the plurality of test physiological signals respectively; and, the processing circuit is arranged for:
  selecting the optimal test physiological signal among the plurality of test physiological signals;
  calculating a plurality of test estimations of the physiological feature of the specific user according to the plurality of test physiological signals;
  calculating the plurality of compensation parameters corresponding to the plurality of test physiological signals excluding the optimal test physiological signal by comparing a test estimation of the optimal test physiological signal with a test estimation of each different test physiological signal; and
  establishing and storing the profile of the physiological feature of the specific user in a memory circuit according to the plurality of test physiological signals and the plurality of compensation parameters corresponding to the plurality of test physiological signals excluding the optimal test physiological signal.

12. The physiological sensor device of claim 11, wherein the processing circuit is arranged to select the optimal test physiological signal according to a slope change of values neighboring to a peak value of each test physiological signal.

13. The physiological sensor device of claim 11, wherein the plurality of observations for the physiological feature of the user corresponds to a plurality of different pressures touched by the specific user for the physiological sensor device.

14. The physiological sensor device of claim 10, wherein the physiological feature of the specific user indicates a blood pressure of the specific user.

15. A physiological sensor device for establishing a profile of a physiological feature of a specific user, comprising:
  a physiological sensor, configured to operate under a test sensing mode to sense the physiological feature of the specific user to obtain a plurality of observations for the physiological feature to generate a plurality of test physiological signals respectively; and
  a processing circuit, coupled to the physiological sensor, configured for:
    selecting an optimal test physiological signal among the plurality of test physiological signals;
    calculating a plurality of test estimations of the physiological feature of the specific user according to the plurality of test physiological signals;
    calculating a plurality of compensation parameters corresponding to a plurality of non-optimal test physiological signals in the plurality of test physiological signals by comparing a test estimation of the optimal test physiological signal with a test estimation of each different non-optimal test physiological signal; and
    establishing and storing the profile of the physiological feature of the specific user in a memory circuit according to the plurality of test physiological signals and the plurality of compensation parameters corresponding to the plurality of non-optimal test physiological signals;
  wherein the profile of the physiological feature of the specific user comprises the plurality of test physiological signals, the plurality of compensation parameters, and the optimal test physiological signal; the plurality of non-optimal test physiological signals in the plurality of test physiological signals are respectively generated in response to different pressures asserted by the specific user on the physiological sensor device, and the plurality of compensation parameters are respectively associated with the different pressures asserted by the specific user; and, a compensation parameter corresponding to a non-optimal test physiological signal is used to compensate a preliminary estimation of the physiological feature of the specific user under a normal sensing mode, and the preliminary estimation is calculated according to the non-optimal test physiological signal.

16. The physiological sensor device of claim 15, wherein the processing circuit is arranged to select the optimal test physiological signal according to a slope change of values neighboring to a peak value of each test physiological signal.

17. The physiological sensor device of claim 15, wherein the physiological sensor device further transmits the profile of the physiological feature of the specific user to a remote system so that the remote system grades the physiological feature of the specific user by comparing the profile of the physiological feature of the specific user with profile(s) of the physiological feature of other different user(s).

18. A system for establishing profiles corresponding to a physiological feature of different users, comprising:
- a first physiological sensor device, for operating under a test sensing mode to sense the physiological feature of a first user to obtain a plurality of observations for the physiological feature of the first user to generate a plurality of first test physiological signals respectively;
- a second physiological sensor device, for operating under the test sensing mode to sense the physiological feature of a second user to obtain a plurality of observations for the physiological feature of the second user to generate a plurality of second test physiological signals respectively; and
- a processor, for establishing a first profile corresponding to the physiological feature of the first user according to the plurality of first test physiological signals, establishing a second profile corresponding to the physiological feature of the second user according to the plurality of second test physiological signals, and assigning different grades to the physiological feature of the first user and the physiological feature of the second user according to the first profile and the second profile respectively;
- wherein the first profile comprises the plurality of first test physiological signals, first compensation parameters of a plurality of non-optimal first test physiological signals in the plurality of first test physiological signals, and an optimal first test physiological signal in the plurality of first test physiological signals; the plurality of non-optimal first test physiological signals in the plurality of first test physiological signals are respectively generated in response to different pressures asserted by the first user on the first physiological sensor device, and the first compensation parameters are associated with the different pressures asserted by the first user; the second profile comprises the plurality of second test physiological signals, second compensation parameters of a plurality of non-optimal second test physiological signals in the plurality of second test physiological signals, and an optimal second test physiological signal in the plurality of second test physiological signals; the plurality of non-optimal second test physiological signals in the plurality of second test physiological signals are respectively generated in response to different pressures asserted by the second user on the second physiological sensor device, and the second compensation parameters are associated with the different pressures asserted by the second user; when a matched physiological signal, which is determined from the plurality of first test physiological signals, is the optimal test physiological signal, a resultant estimation of the physiological feature of the first user is calculated according to the matched physiological signal; and, when the matched physiological signal is a non-optimal test physiological signal and in the plurality of test physiological signals and different from the optimal test physiological signal, a preliminary estimation of the physiological feature of the first user is calculated according to the non-optimal test physiological signal, and then the preliminary estimation is compensated by referring to a compensation parameter corresponding to the non-optimal test physiological signal without using the optimal test physiological signal so as to generate the resultant estimation of the physiological feature of the first user.

* * * * *